United States Patent
Salmi et al.

(10) Patent No.: US 6,593,502 B2
(45) Date of Patent: Jul. 15, 2003

(54) PROCESS FOR THE PREPARATION OF POLYOLS

(75) Inventors: Tapio Salmi, Turku (FI); Valentina Serra-Holm, Turku (FI); Tiina-Kaisa Rantakylä, Turku (FI); Päivi Mäki-Arvela, Turku (FI); Lars-Peter Lindfors, Espoo (FI); Hannu Nousiainen, Porvoo (FI)

(73) Assignee: Dynea Chemicals Oy, Helsinki (FI)

( * ) Notice: Subject to any disclaimer, the term of this patent is extended or adjusted under 35 U.S.C. 154(b) by 0 days.

(21) Appl. No.: 10/038,597

(22) Filed: Jan. 2, 2002

(65) Prior Publication Data

US 2002/0151754 A1 Oct. 17, 2002

Related U.S. Application Data

(63) Continuation of application No. PCT/FI00/00602, filed on Jun. 30, 2000.

(30) Foreign Application Priority Data

Jul. 2, 1999 (FI) .................................................. 991519

(51) Int. Cl.[7] .......................... C07C 27/04; C07C 31/18; C07C 29/14; C07C 27/00; C07C 29/00
(52) U.S. Cl. ......................... 568/862; 568/863; 568/852; 568/881; 568/853; 568/880
(58) Field of Search ................................. 568/862, 863, 568/852, 881, 853, 463, 464, 458, 457, 880

(56) References Cited

FOREIGN PATENT DOCUMENTS

WO    WO 98/29374    * 7/1998

* cited by examiner

Primary Examiner—Samuel Barts
Assistant Examiner—Elvis O. Price
(74) Attorney, Agent, or Firm—Scully, Scott, Murphy & Presser

(57) ABSTRACT

The invention relates to a process for the preparation of polyols having 3 or 4 hydroxyl groups, from an aldehyde and formaldehyde in the presence of water, followed by hydrogenation of the aldolisation product in the presence of a hydrogenation catalyst at an elevated temperature. The aledhyde is obtained by an aldolisation reaction of an aldehyde having at least two α-hydrogen atoms and a formula according to $R_1CH_2CHO$, wherein $R_1$ is selected from a group comprising hydrogen, alkyl groups having 1–7 carbon atoms which can have cycloalkyl substituents, cycloalkyl groups, aryl groups and aralkyl groups with 1–7 carbon atoms is the alkyl chain, with formaldehyde in the presence of water in an amount of 20–70 wt %, preferably 40–60 wt % and in the presence of an anion exchange resin. The hydrogenation is preferably carried out in the presence of water.

13 Claims, 3 Drawing Sheets

PROCESS FOR THE PREPARATION OF POLYOLS

This is a continuation of PCT Application No. PCT/FI00/00602 dated Jun. 30, 2000.

The invention relates to a process for the preparation of polyols having 3 or 4 hydroxyl groups, from an aldehyde and formaldehyde in the presence of water, followed by hydrogenation of the aldolisation product in the presence of a hydrogenation catalyst at an elevated temperature.

Polyols and especially 1,1,1-trimethylolpropane (TMP) are important starting materials and intermediates in the production of synthetic resins, such as polyester resins and the like. They may also be used in the manufacture of plasticizers, synthetic lubricants, surfactants etc. Polyols like 1,1,1-trimethylolpropane are prepared by allowing formaldehyde and another aldehyde to react in the presence of a strongly alkaline catalyst, such as sodium hydroxide, potassium hydroxide or calcium hydroxide to form a desired alcohol. However, large amounts of formate salts are formed as by-products thus making the process not very attractive for commercial purposes. In another, alternative process the aldolisation reaction of formaldehyde and another aldehyde is carried out in the presence of an amine catalyst, such as triethylamine, followed by hydrogenation. The aldolisation reaction may also be performed with an anion exchange resin acting as a catalyst.

A method for the manufacture of polyalcohols is presented in DE 19542036, wherein an alkanal or ketone is allowed to react with formaldehyde in an aqueous solution in the presence of an amine, then water, excess of amine, excess of formaldehyde and methanol formed from Cannizzarro-reaction with formaldehyde are separated. The remaining reaction mixture is heated and polyalcohol formate is formed. The obtained polyalcohol formate is subjected to trans-esterification with an alcohol in order to obtain the desired polyalcohol, which is isolated from the reaction mixture.

In U.S. Pat. No. 5,144,088 is disclosed a process for the manufacture of a polyol, and especially neopentyl glycol wherein isobutyraldehyde is reacted with paraformaldehyde in the presence of a tertiary amine, preferably triethylamine and of one or more oxides of elements of groups IB, IVA, IVB, VA, VB, VIB and VII of the periodic table and then hydrogenating the obtained monomeric and dimeric hydroxypivaldehyde.

In U.S. Pat. No. 5,146,012 is described a method of making neopentyl glycol by reacting isobutyraldehyde with paraformaldehyde to obtain a reaction product comprising hydroxypivaldehyde, forming a mixture of the reaction product with about 40–90% of an alcohol, preferably methanol and then contacting the mixture with hydrogen in the presence of a hydrogenation catalysts.

A process for the manufacture of polyols is disclosed in FI 965268 wherein an aldolisation reaction is performed with formaldehyde and another aldehyde comprising at least 2 carbon atoms, in the presence of a weakly basic anion exchange resin, followed by hydrogenation which is performed in the presence of a solvent and a hydrogenation catalyst.

A process is disclosed in FI 974638 for the preparation of neopentyl glycol by hydrogenation of hydroxypivaldehyde in the presence of hydrogen and a hydrogenation catalyst containing nickel, at a temperature below 100° C. in a liquid phase comprising a solvent in an amount of 1–70 wt %, preferably an aliphatic alcohol or ether or a mixture thereof and water in an amount of less than 15 wt %.

A method is disclosed in JP 10287606 for the purification of dimethylol alkanal. Unreacted formaldehyde is separated from a reaction product containing dimethylol alkanal, obtained by carrying out a condensation reaction of an aliphatic aldehyde with formaldehyde in the presence of a hydroxide, a carbonate or a bicarbonate of an alkali metal or an alkaline earth metal, or other basic catalyst, such as anion exchange resin and water. Water is added to the reaction product solution so that the water amount is about 4 times by weight, based on the formaldehyde content in the reaction product solution, then the mixture is fed to a thin-film type vaporizer to concentrate the solution and the thus generated formaldehyde vapour and steam are distilled away from one end of the thin-film type vaporizer to purify the dimethylol alkanal.

It has been observed that several problems are related to the methods according to the state of the art. For example, in the first step of the manufacturing process of 1,1,1-trimethylolpropane (TMP), the aldolisation step of the aldehydes, undesired side reactions may occur. When the starting material, such as n-butanal, reacts with formaldehyde, 2-ethyl-3-hydroxypropanal is formed but also as a result of dehydration 2-ethylpropenal (ethyl acrolein) is obtained. 2-Ethyl-3-hydroxypropanal further reacts with formaldehyde to yield the desired intermediate 2-ethyl-3-hydroxy-2-(hydroxymethyl)propanal (TMPA). Because of the side reactions, the yield of the aldol in the aldolisation step and further the yield and purity of the final product are lower. The aldol product 2-ethyl-3-hydroxy-2-(hydroxymethyl)propanal contains varying amounts of unreacted formaldehyde which is a catalyst inhibitor affecting the subsequent catalytic hydrogenation step. To compensate the inhibiting effect of formaldehyde on the hydrogenation reaction, large amounts of the hydrogenation catalyst must be used thus increasing the reactor size and investment costs. Usually, the number of phases of a component depends on the temperature and concentration. If formaldehyde concentration increases, especially at low temperatures below 50° C., solid paraformaldehyde is formed, which can cause severe blocking problems in the process. Based on the above it can be seen that there clearly exists a need for an improved process for the manufacture of polyols with improved yields, purity, conversion and selectivity.

The invention relates to a process for the preparation of polyols by aldolisation of an aldehyde with formaldehyde over an anion exhange resin catalyst, followed by hydrogenation of the aldol product over a supported metal catalyst.

Characteristic features of the process for the preparation of polyols are stated in the claims.

It has been observed that above mentioned objectives can be achieved and the disadvantages of the methods according to the state of the art can be avoided by the method according to the invention. Polyols may conveniently be produced by performing an aldolisation reaction followed by hydrogenating the aldol product. The aldolisation reaction is preferably carried out in the presence of water and in the presence of an anion exchange resin and in a substantially alcohol-free environment and the subsequent hydrogenation of the aldol product is performed preferably in the presence of water.

In the process according to the invention for the preparation of polyols having 3 or 4 hydroxyl groups, an aldehyde is obtained by aldolisation reaction of an aldehyde having at least two α-hydrogen atoms and a formula according to $R_1CH_2CHO$ wherein $R_1$ is selected from a group comprising hydrogen, alkyl groups having 1–7 carbon atoms which can have cycloalkyl substituents, cycloalkyl groups, aryl groups and aralkyl groups with 1–7 carbon atoms in the alkyl chain, with formaldehyde in the presence of water in an amount of 20–70 wt %, preferably 40–60 wt %, and the obtained aldehyde is hydrogenated.

The substantially alcohol-free environment means that the aldolisation reaction is carried out in the presence of methanol in an amount of 0–20 wt %, preferably 0–12 wt %. In the aldolisation reaction an aldehyde having at least two α-hydrogen atoms and formaldehyde are reacted in the presence of an anion exchange resin with a molar ratio of formaldehyde to the aldehyde of 2:1–6:1 and at a temperature of 15–100° C., preferably 50–70° C.

Any suitable anion exchange resin catalyst may be applied, preferably weakly basic anion exchange resins, and the upper limit for the reaction temperature is limited by the thermal resistance of the anion exchange resin used. Preferable the anion exchange resins comprise functional groups which are selected from primary amines (—$NH_2$), secondary amines (—NHR where R is an alkyl or an aryl group), tertiary amines (—$NR_2$, where R is as above and R can be same or different alkyl group), and combinations thereof The resin matrix used may suitably be a condensation product of epichloro-hydrine with an amine or ammonia, a phenolic resin, an acrylic resin or a styrene copolymer, such as chloromethylated styrene-divinyl benzene copolymer. Suitable weakly basic anion exhange resins are disclosed in FI 965268.

The aldolisation reaction is carried out preferably under an inert atmosphere, such as nitrogen atmosphere, and it can be carried out as a batch process, as a semibatch process or preferably as a continuous process.

Figure 1:
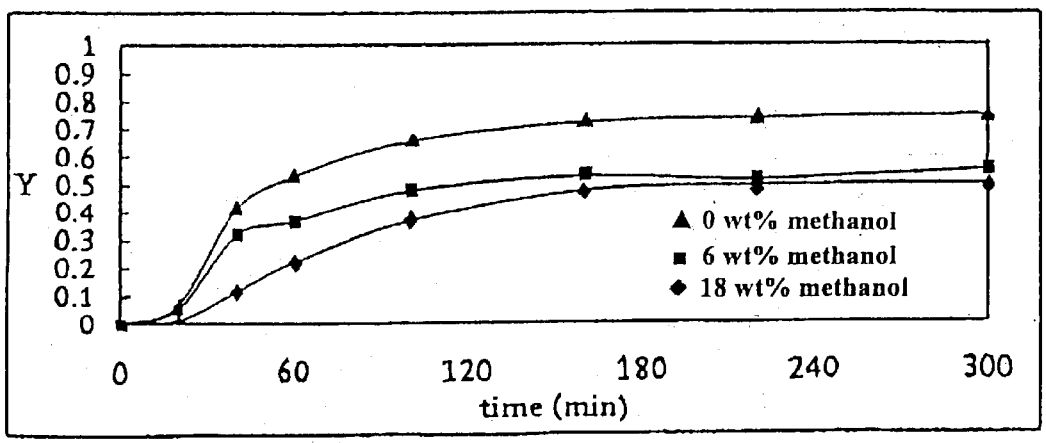
FIG. 1 is a graph illustrating the effect of methanol on the TMP-aldol yield (Y).

The effect of methanol on the TMP-aldol yield (Y) is presented in FIG. 1. Three different experiments were carried out with 0, 6, and 18 wt % of methanol. The experiment in the absence of methanol was carried out with paraformaldehyde.

The graph of FIG. 1 illustrates TMP-aldol yield (Y) in the presence of 18 wt % of methanol (♦), 6 wt % of methanol (■), 0 wt % of methanol (▲) and with a formaldehyde-to-aldehyde molar ratio of 4:1, T=70° C., 55 wt % of water.

Figure 2:
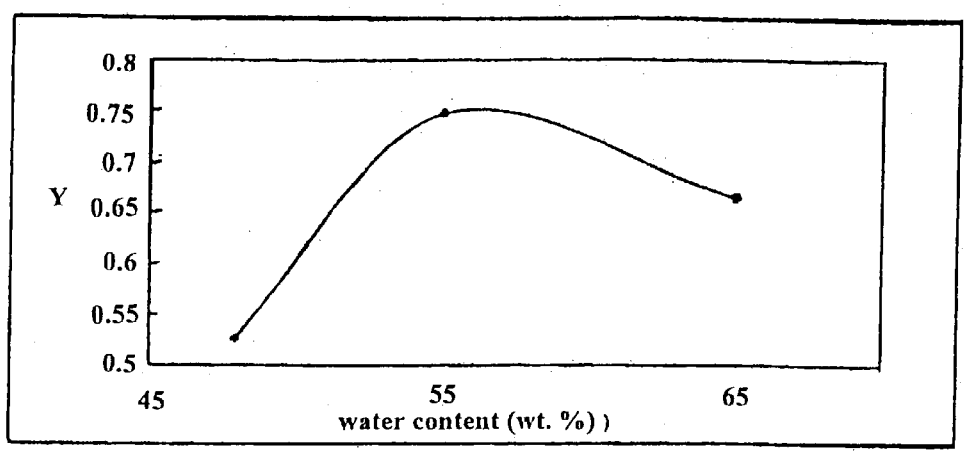
FIG. 2 is a graph illustrating the effect of water on the TMP-aldol yield (Y) in a methanol-free environment.

The effect of water content on the TMP-aldol yield (Y) in a methanol-free environment is presented in FIG. 2. It can be seen that the yield of the aldol CV) after 5 hours at 70° C. with a formaldehyde-to-aldehyde molar ratio of 4:1 for three different water concentration values reaches a maximum value with 55 wt % of water in the reaction mixture.

After the aldolisation step the aldol product is hydrogenated. The hydrogenation is carried out at a temperature of 50–200° C., preferably at 60–90° C. and under a pressure of 1–200 bar, preferably 10–80 bar. Solvents may optionally be used in the hydrogenation and suitable solvents are aliphatic alcohols, such as methanol, ethanol and propanol in an amount of 0–70 wt %, preferably 30–50 wt %.

However, in the case the aldolisation mixture, after the aldolisation step, contains formaldehyde, it was found that with using Ni-catalyst as the hydrogenation catalyst it is advantageous to use only water as a solvent instead of alcohols in the hydrogenation of the aldol product. Normally formaldehyde retards the hydrogenation of the aldol product but when using only water as a solvent, the hydrogenation rate of the aldol product increases noticeably. A suitable water concentration is 0–90 wt %, preferably 20–90 wt %.

The aldol product may also optionally be purified before hydrogenation by steam distillation, wherein the obtained aldolisation reaction mixture and water are mixed and distillation is carried out. Water, formaldehyde and impurities are co-distilled. Alternatively, steam may also be directly passed into the liquid to be distilled. The separation of formaldehyde and impurities, such as ethylacrolein, from the aldol product by steam distallation is preferably performed in vacuum or under atmospheric pressure and typically at a temperature of 50–110° C. The unreacted formaldehyde separated from the aldol product can be recycled back to the aldolisation reactor thus dereasing the formaldehyde consumption and increasing the efficiency of the overall process.

As a hydrogenation catalyst a commercial catalyst such as a supported metal catalyst may be used comprising Cu, Cr, Ni, Zn, Pt, Pd, Ru, Mn or Co. Suitable catalysts are Cu—Zn/$Al_2O_3$, Cu—Cr/$Al_2O_3$, Ni/$SiO_2$, Ni—Cr/$SiO_2$, Pt/C, Pt—Pd/C, Ru/C and Ru—Pd/C, and preferable ones are Cu—Cr/$Al_2O_3$ and Ni—Cr/$SiO_2$. The amount of nickel in the catalyst may be 60–99 wt % and the amount of chromium may be 1–40 wt %. When the reaction mixture from the aldolisation step contains formaldehyde and the hydrogenation step is performed in water, Ni-catalyst is a preferable choice. The catalyst may be combined with a suitable carrier which can be an inorganic oxide such as silica or carbon. The catalyst may optionally be activated before the hydrogenation, preferably at a temperature of about 400° C. in hydrogen flow. The hydrogenation step may be carried out as a batch process, as a semi-batch process or preferably as a continuous process. After the hydrogenation step, the desired polyol is separated from the reaction mixture by any suitable method, such as distillation, and the solvents used may be recycled to the hydrogenation step.

The method according to the invention has several advantages. The aldolisation reaction is performed using a solid catalyst, and thus no separation of the catalyst after the reaction and no recycling of the catalyst are required. The process for the manufacture of polyols exhibits improved selectivity and good conversion due to the optimum amount of water in the aldolization step. In the case of 1,1,1-trimethylolpropane, the formation of ethylacrolein can be reduced by optimizing the amount of water in the reaction mixture. By using water as solvent in the hydrogenation step, the performance of the hydrogenation step is improved because surprisingly no catalyst inhibiting effect of formaldehyde occurs and thus less hydrogenation catalyst is needed. The process is very effective and economic because complete removal of formaldehyde is not required after the aldolisation step, and the hydrogenation process in water works with smaller and larger amounts of formaldehyde equally well. The improved selectivity of the aldolisation step in the presence of a weakly basic anion exchange resin, the improved performance of the hydrogenation step and the improved overall yield of the crude product make the process economically advantageous, because as a result the raw material consumption is decreased and also the purification costs of the final product will decrease.

In the following, the invention is described in more detail with reference to the accompanying examples which are nevertheless not intended as limiting the invention

EXAMPLES 1–7

Aldolisation

Seven experiments were made using formaldehyde and n-butyraldehyde as starting materials. Different methanol and water concentrations in the feed mixture were used to study the effect of solvent or bisolvent on the aldolisation reaction. Experimental conditions and results for aldolisation are presented in following Table 1.

TABLE I

Experimental conditions and results of aldolisation

|  | Experiment 1 | Experiment 2 | Experiment 3 | Experiment 4 | Experiment 5 | Experiment 6 | Experiment 7 |
|---|---|---|---|---|---|---|---|
| Catalyst* mass (g) | 160 | 160 | 160 | 160 | 160 | 160 | 160 |
| Mass of the liquid phase (g) | 759 | 711 | 743 | 754 | 748 | 714 | 735 |
| Temperature (° C.) | 70 | 50 | 60 | 70 | 70 | 70 | 70 |
| FH-to-BAL molar ratio | 4 | 3 | 2 | 4 | 4 | 4 | 4 |
| Experiment duration (h) | 5 | 6 | 5 | 5 | 5 | 5 | 5 |
| BAL feed (g) | 130 | 142 | 180 | 148 | 98 | 72 | 109 |
| FH feed (g) | 223 | 219 | 163 | 327 | 212 | 286 | 429 |
| Extra water feed (g) | 310 | 251 | 306 | 184 | 342 | 159 | 100 |
| Extra methanol feed (g) | 0 | 0 | 0 | 0 | 0 | 100 | 0 |
| Water wt.-% | 55 | 55 | 55 | 48 | 65 | 55 | 55 |
| Methanol wt.-% | 0 | 0 | 0 | 0 | 0 | 18 | 6 |
| Yield of aldol (Y) | 0.75 | 0.61 | 0.59 | 0.53 | 0.67 | 0.50 | 0.48 |
| Yield of ethyl acrolein (Y) | 0.23 | 0.32 | 0.34 | 0.23 | 0.23 | 0.24 | 0.26 |
| Final concentration of FH (wt %) | 15.2 | 12.6 | 6.15 | 17.1 | 14.3 | 10.3 | 13.5 |
| Final concentration of BAL (wt %) | 0.2 | 1.5 | 1.8 | 0.8 | 0.2 | 0.4 | 0.7 |
| Final concentration of TMPA (wt %) | 22.4 | 17.6 | 24.3 | 15.3 | 12.7 | 8.5 | 12.2 |
| Final concentration of EA (wt %) | 4.4 | 5.9 | 9.0 | 4.3 | 2.8 | 2.8 | 4.2 |

Note: In the runs without methanol, formaldehyde was introduced in the system as paraformaldehyde, while in the runs with methanol 42 wt % formalin was used. The amounts reported are therefore referred to paraformaldehyde for experiments 1–5 and to formalin for experiments 6 and 7. In experiments 4 and 5 paraformaldehyde contains 25 wt % of water.
FH = formaldehyde
BAL = n-butyraldehyde
TMPA = 2-ethyl-3-hydroxy-2-(hydroxymethyl)propanal
EA = ethylacrolein
*commercial weak anion exhange resin was used in each example

EXAMPLES 8–16

Several commercial anion exchange resins were tested as aldolisation catalysts. The main properties of resins are listed in Table II. The values of selectivity (s) towards aldol, defined as the ratio of the yield of aldol to the yield of ethylacrolein, are also reported. Experiments were carried out at 60° C. with a formaldehyde-to-butyraldehyde molar ratio of 4:1 and values were calculated after 6 hours of reaction.

TABLE II

Anion exchange resins used as aldolisation catalysts

| Example | Matrix | Type | Funcs | Capacity, Mol/L | Max. T, ° C. | s |
|---|---|---|---|---|---|---|
| 8 | Polystyrene-DVB | Macro | —N(CH$_3$)$_3$ | 1.0 | 60 | 6.0 |
| 9 | Polystyrene-DVB | Macro | —N(CH$_3$)$_3$ | 1.08 | Na | 5.0 |
| 10 | Acrylic-DVB | Gel | NR$_2$ | 1.6 | 75 | 3.3 |
| 11 | Acrylic-DVB | Macro | NR$_2$ | 1.6 | Na | 6.1 |
| 12 | Polystyrene-DVB | Macro | NR$_2$ | 1.25 | 100 | 2.6 |
| 13 | Polystyrene-DVB | Macro | NR$_2$ | 1.6 | 60 | 3.9 |
| 14 | Polystyrene-DVB | Macro | NR$_2$ | 1.3 | Na | 2.5 |
| 15 | Polystyrene-DVB | Macro | NR$_2$ | 1.7 | 100 | 4.5 |
| 16 | Polystyrene-DVB | Macro | NR$_2$ | 1.5 | 100 | 2.8 |

EXAMPLE 17

Purification of aldol product 2-ethyl-3-hydroxy-2-hydroxymethyl) propanal

The separation of formaldehyde from the aldol product was performed under atmospheric pressure and at 100° C. using a total batch volume of 400 ml (200 ml of aldolization product mixed with 200 ml of distilled water). Immediately as the first distilled droplets from the condenser were observed the addition of extra water was commenced. The water feeding was adjusted in order to maintain a constant liquid volume in the distillation flask. Reducing of the formaldehyde content from 4.5 wt % to under 1.0 wt % required 750 ml water fed through the distillation pot. The distillation time was 3 hours. Lowering of the formaldehyde content under 0.2 wt % required 1600 ml of water fed through the distillation pot, and the distillation time was 7 hours. After the distillation 200 ml of water was evaporated from the solution to remove the water which was added before the distillation.

Ethylacrolein, the dominant co-product from the aldolization step, was also distilled away in the separation step.

EXAMPLES 18–19

Hydrogenation of the purified aldol product to 1,1, 1-tri-methylolpropane (1,1,1-tri(hydroxymethyl) propane)

Two experiments with different formaldehyde concentrations 0.19 wt % and 0.93 wt % in the feed were performed. The experiments were performed in a pressurized batch reactor to which a bubbling unit was connected.

5 g of commercial Ni-catalyst was placed into a reactor. The pressure was adjusted to 2 bar and the hydrogen flow to 500 ml/min. After the desired activation temperature (400° C.) was achieved the hydrogen flow was increased to 750 ml/min and the catalyst was activated. Then 150 ml of aldol product, from which formaldehyde and ethylacrolein were separated, and 150 ml of methanol were mixed. The feed mixture was poured into the bubbling unit where it was saturated with hydrogen during 10–15 minutes in order to remove oxygen from the solution. The pressure in the reactor was reduced from 2 bar to 1.5 bar while the pressure in the bubbling unit was increased to 8 bar and the feed mixture was injected into the reactor. The desired pressure (70 bar) and temperature (90° C.) were adjusted and the hydrogen feed was introduced. When the temperature was 15–20° C. below the desired one, the agitation was switched on and adjusted to 1000 rpm. The samples taken during the process were analyzed using HPLC and GC. The operating conditions in the experiments and the results obtained are summarized as follows:

| Example 18: | | |
|---|---|---|
| Catalyst: | Commercial Ni-catalyst | |
| Particle size: | 45–150 µm | |
| Catalyst mass: | 5 g | |
| Liquid volume: | 300 ml | |
| Temperature: | 90° C. | |
| Pressure: | 70 bar | |
| Stirring speed: | 1000 rpm | |
| Feed mixture: | Formaldehyde | 0.19 wt % |
| | Aldol product | 14.55 wt % |
| | MeOH+H$_2$O | 85.26 wt % |
| Product: | 1,1,1-Trimethylolpropane | 14.67 wt % |
| | MeOH+H$_2$O | 85.33 wt % |
| Conversion: | 100% | |
| Selectivity: | 99% | |
| Example 19: | | |
| Catalyst: | Commercial Ni-catalyst | |
| Particle size: | 45–150 µm | |
| Catalyst mass: | 5 g | |
| Liquid volume: | 300 ml | |
| Temperature: | 90° C. | |
| Pressure: | 70 bar | |
| Stirring speed: | 1000 rpm | |
| Feed mixture: | Formaldehyde | 0.93 wt % |
| | Aldol product | 13.14 wt % |
| | MeOH+H$_2$O | 85.93 wt % |
| Product: | 1,1,1-Trimethylolpropane | 12.15 wt % |
| | MeOH+H$_2$O + uic | 87.85 wt % |
| | (uic = unidentified components) | |
| Conversion: | 100% | |
| Selectivity: | 91% | |

Figure 3:
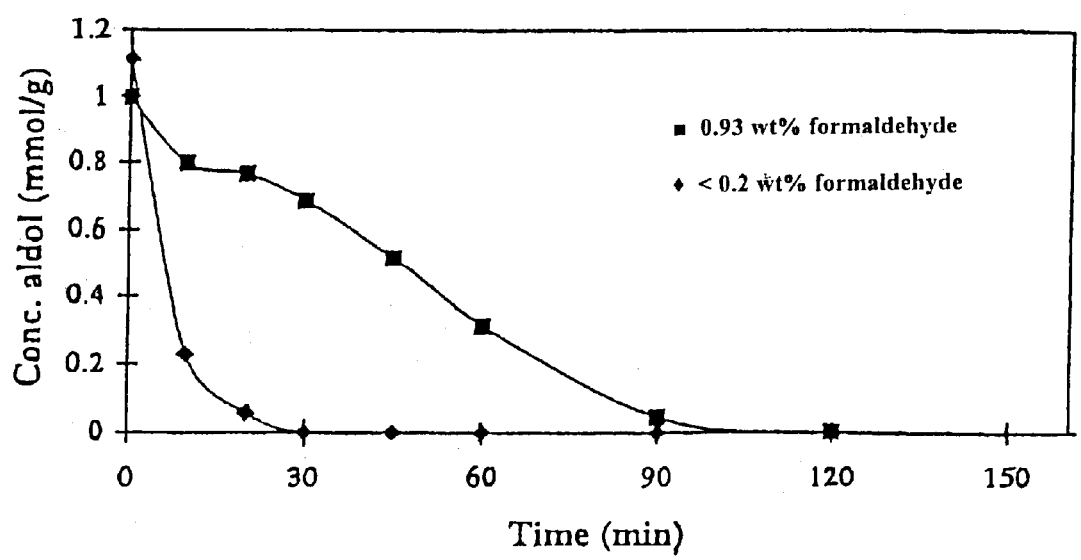
FIG. 3 is a graph illustrating the effect of formaldehyde concentration on the hydrogenation of aldol.

In the experiment (Ex. 18) carried out with a feed that had a very low formaldehyde content (<0.2 wt %) the hydrogenation rate was significantly higher in the beginning, and no retardation was observed. This indicates strong inhibiting effect of formaldehyde, which can be seen from the graph illustrated in FIG. 3. An initial retardation of the reaction rate at the temperature of 90° C. was observed when the formaldehyde content of the feed was 0.93 wt %. (Ex. 19). FIG. 3 illustrates the effect of formaldehyde concentration, 0.93 wt % (-■-) example 19, compared with less tan 0.2 wt % (-♦-) example 18, on the hydrogenation of aldol at 90° C. and 70 bar.

Influence of Solvent on the Hydrogenation of TMP-aldol

EXAMPLES 20–26

First, 5 g of crushed and sieved (particle size<45 µm) commercial Ni-catalyst was placed into the reactor and activated at 400° C. under hydrogen flow for 1 h.

Secondly, a hydrogenation feed was poured into the bubbling unit where it was saturated with hydrogen in 10 minutes in order to remove oxygen from the solution. After the oxygen removal, the reaction mixture was pushed into the autoclave. The pressure and temperature were adjusted, and when the target values were achieved, the magnetic stirrer was switched on and the agitation velocity was adjusted. Liquid samples were withdrawn and analyzed.

Figure 4:
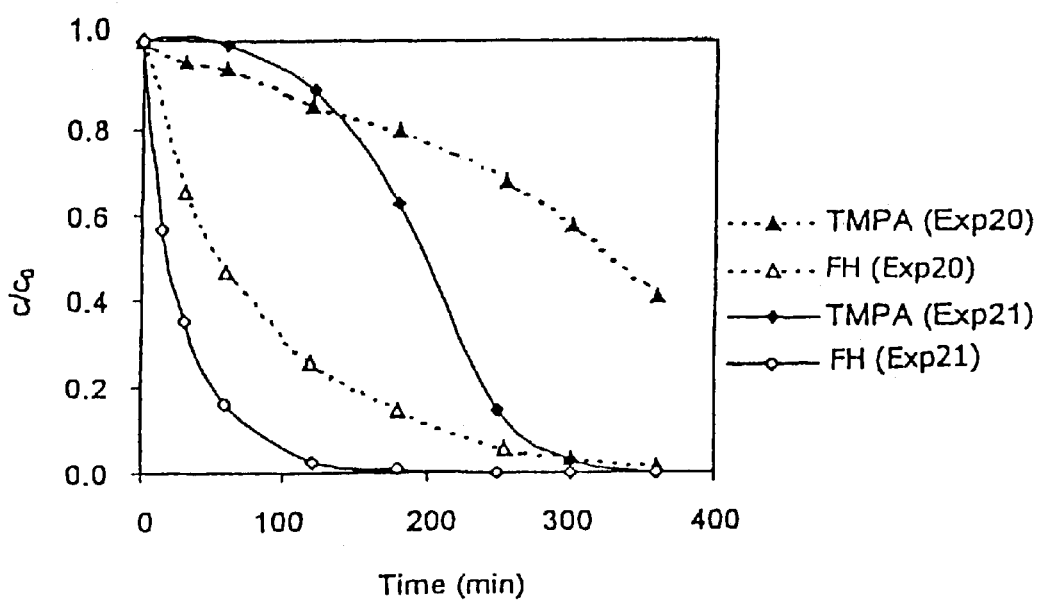
FIG. 4 is a graph illustrating the hydrogenation of TMP-aldol with high FH-content
Figure 5:
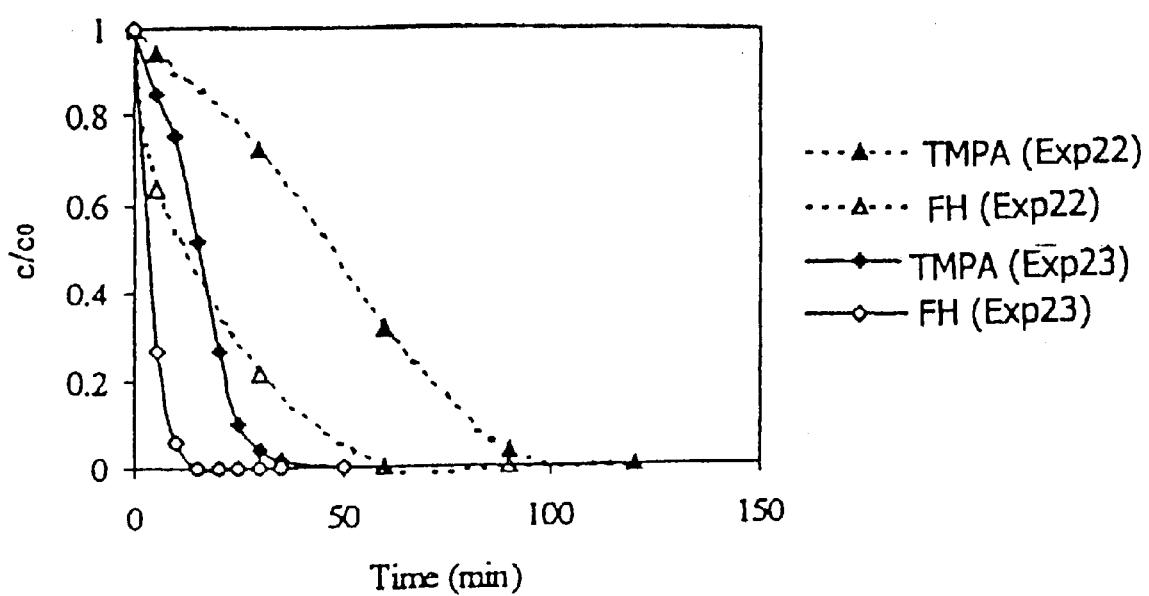
FIG. 5 is a graph illustrating the hydrogenation of TMP-aldol with low initial FH-content.

The superiority of pure water as a solvent when high initial formaldehyde (FH) content was is to illustrated in FIGS. 4 and 5. In examples 24 to 26 the hydrogenation performed in different process conditions using water as the solvent. The process conditions and results of experiments are summarized as follow:

| Examples 20–23 Comparison of water and methanol as solvents in the hydrogenation | | |
|---|---|---|
| Example 20 (methanolic solvent) | | |
| Catalyst: | Commercial Ni-catalyst | |
| Particle size: | <45 µm | |
| Catalyst mass: | 5 g | |
| Liquid volume: | 300 ml | |
| Temperature: | 80° C. | |
| Pressure: | 80 bar | |
| Stirring speed: | 1500 rpm | |
| Feed mixture: | FH | 2.17 wt % |
| | TPM-aldol | 9.90 wt % |
| | TMP | 1.03 wt % |
| | MeOH | 42.0 wt % |
| | H$_2$O | 44.9 wt % |
| Product: | TMP | 7.44 wt % |
| | TMP-aldol | 4.04 wt % |
| | FH | 0.04 wt % |
| | MeOH* | 43.6 wt % |
| | H$_2$O | 44.9 wt % |
| Convefsion at 360 min: | | 59% |
| Selectivity: | | 100% |
| Example 21 (non-methanolic solvent): | | |
| Catalyst: | Commercial Ni-catalyst | |
| Particle size: | <45 µm | |
| Catalyst mass: | 5 g | |
| Liquid volume: | 300 ml | |
| Temperature: | 80° C. | |
| Pressure: | 80 bar | |
| Stirring speed: | 1500 rpm | |
| Starting mixture: | FH | 2.27 wt % |
| | TPM-aldol | 11.11 wt % |
| | TMP | 0.68 wt % |
| | MeOH | 0.3 wt % |
| | H$_2$O | 85.64 wt % |
| Product: | TMP | 12.74 wt % |
| | TMP-aldol | 0 wt % |
| | FH | 0 wt % |
| | MeOH* | 1.6 wt % |
| | H$_2$O | 85.64 wt % |

-continued

| Examples 20–23 Comparison of water and methanol as solvents in the hydrogenation | |
|---|---|
| Conversion at 360 min: | 100% |
| Selectivity: | 100% |

*MeOH produced in hydrogenation reaction of FH

The results of Examples 20 and 21 are illustrated in the graph of FIG. 4, said graph showing the hydrogenation of TMP-aldol at 80° C. and 80 bar with high PH-content (over 2 wt %) using a mixture of MeOH and $H_2O$ or pure water as a solvent.

| Example 22 (methanolic solvent): | | | |
|---|---|---|---|
| Catalyst: | Commercial Ni-catalyst | | |
| Particle size: | 45–150 μm | | |
| Catalyst mass: | 5 g | | |
| Liquid volume: | 300 ml | | |
| Temperature: | 90° C. | | |
| Pressure: | 80 bar | | |
| Stirring speed: | 1500 rpm | | |
| Starting mixture: | FH | 0.99 wt % | |
| | TPM-aldol | 12.18 wt % | |
| | TMP | 0.87 wt % | |
| | MeOH + $H_2O$ | 85.96 wt % | 50% MeOH 35, 96% $H_2O$ |
| Product: | TMP | 13.5 wt % | |
| | MeOH + $H_2O$ | 86.5 wt % | |
| Conversion at 120 min: | | 100% | |
| Selectivity: | | 100% | |
| Example 23 (non-methanolic solvent): | | | |
| Catalyst: | Commercial Ni-catalyst | | |
| Particle size: | 45–150 μm | | |
| Catalyst mass: | 5 g | | |
| Liquid volume: | 300 ml | | |
| Temperature: | 90° C. | | |
| Pressure: | 80 bar | | |
| Stirring speed: | 1500 rpm | | |
| Starting mixture: | FH | 0.63 wt % | |
| | TPM-aldol | 10.80 wt % | |
| | TMP | 1.22 wt% | |
| | $H_2O$ | 87.35 wt % | |
| Product: | TMP | 12.50 wt % | |
| | $H_2O$ + MeOH | 87.5 wt % | |
| Conversion at 50 min: | | 100% | |
| Selectivity: | | 100% | |

*MeOH produced in hydrogenation reaction of FH

The result of Example 22 and 23 are illustrated in the graphs showing FIG. 5, said graph showing the hydrogenation of TMP-aldol at 90° C. and 80 with low initial FH-content (below 1 wt %) using a mixture of MeOH and $H_2O$ or pure water as a solvent.

| Example 24 (non-methanolic solvent): | | |
|---|---|---|
| Catalyst: | Commercial Ni-catalyst | |
| Particle size: | 45–150 μm | |
| Catalyst mass: | 5 g | |
| Liquid volume: | 300 ml | |
| Temperature: | 90° C. | |
| Pressure: | 80 bar | |
| Stirring speed: | 1500 rpm | |
| Starting mixture: | FH | 2.25 wt % |

-continued

| | | |
|---|---|---|
| | TPM-aldol | 10.83 wt % |
| | TMP | 0.95 wt % |
| | $H_2O$ | 85.97 wt % |
| Product: | TMP | 12.35 wt % |
| | TMP-aldol | 10.13 wt % |
| | $H_2O$ + MeOH* | 87.52 w % |
| Conversion at 290 min: | | 99% |
| Selectivity: | | 100% |
| Example 25 (non-methanolic solvent): | | |
| Catalyst: | Commercial Ni-catalyst | |
| Particle size: | 45–150 μm | |
| Catalyst mass: | 5 g | |
| Liquid volume: | 300 ml | |
| Temperature: | 75° C. | |
| Pressure: | 60 bar | |
| Stirring speed: | 1500 rpm | |
| Starting mixture: | FH | 0.63 wt % |
| | TPM-aldol | 10.78 wt % |
| | TMP | 1.24 wt % |
| | $H_2O$ | 87.37 wt % |
| Product: | TMP | 12.48 wt % |
| | TMP-aldol | 0.15 wt % |
| | $H_2O$ + MeOH* | 87.37 w % |
| Conversion at 80 min: | | 99% |
| Selectivity: | | 100% |
| Example 26 (non-methanolic solvent): | | |
| Catalyst: | Commercial Ni-catalyst | |
| Particle size: | 45–150 μm | |
| Catalyst mass: | 5 g | |
| Liquid volume: | 300 ml | |
| Temperature: | 60° C. | |
| Pressure: | 40 bar | |
| Stirring speed: | 1500 rpm | |
| Starting mixture: | FH | 0.62 wt % |
| | TPM-aldol | 11.20 wt % |
| | TMP | 1.18 wt % |
| | $H_2O$ | 87.0 wt % |
| Product: | TMP | 12.7 wt % |
| | $H_2O$ + MeOH* | 87.3 wt % |
| Conversion at 230 min: | | 100% |
| Selectivity: | | 100% |

*MeOH produced in hydrogenation reaction of FH

What is claimed is:

1. A process of preparing triols and tetrols by aldolization of an aldehyde having at least two α-hydrogen atoms and having a formula of $R^1CH^2CHO$, where $R^1$ is hydrogen, an alkyl having 1 to 7 carbon atoms, an alkyl having 1 to 7 carbon atoms having at least one cycloalkyl substituent, cycloalkyl, aryl or an aralkyl having 1 to 7 carbon atoms in its alkyl chain, with formaldehyde in the presence of anion exchange resin followed by hydrogenation of the aldol product in the presence of a hydrogenation catalyst, the improvement comprising conducting said aldolization at a temperature of 50° C. to 100° C. in the presence of 48% to 65% by weight of water; and conducting said hydrogenation at a temperature of 50° C. to 200° C. in the presence of 20% to 90% by weight of water as the sole solvent.

2. A process in accordance with claim 1 wherein said hydrogenation is performed at a temperature of 60° C. to 90° C.

3. A process in accordance with claim 1 wherein said aldehyde is n-butanal, propanal or acetaldehyde.

4. A process in accordance with claim 1 wherein said ion exchange resin is a weak basic anion exchange resin which includes at least one —$NH_2$, —NHR or —$NR_2$ functional group, where each R is independently alkyl or aryl.

5. A process in accordance with claim 1 wherein said hydrogenation catalyst includes Ni, Cu, Cr, Zn, Pt, Pd, Ru, Co or Mn.

6. A process in accordance with claim 5 wherein said hydrogenation catalyst is a Ni catalyst.

7. A process in accordance with claim 5 wherein said hydrogenation catalyst is supported on a carrier.

8. A process in accordance with claim 6 wherein said nickel hydrogenation catalyst is supported on a carrier.

9. A process in accordance with claim 7 wherein said carrier is carbon or an inorganic oxide.

10. A process in accordance with claim 8 wherein said carrier is carbon or an inorganic oxide.

11. A process in accordance with claim 1 wherein said aldehyde, obtained in said aldolization, is steamed distilled before said hydrogenation.

12. A process in accordance with claim 11 wherein said steam distillation is conducted at a pressure below atmospheric.

13. A process in accordance with claim 12 wherein said steam distillation is performed in vacuo.

* * * * *